United States Patent
Tomlinson et al.

(10) Patent No.: US 9,924,720 B2
(45) Date of Patent: *Mar. 27, 2018

(54) MICROCAPSULES

(71) Applicants: Dow Global Technologies LLC, Midland, MI (US); Rohm and Haas Company, Philadelphia, PA (US)

(72) Inventors: Ian A. Tomlinson, Midland, MI (US); Nicole L. Wagner, Midland, MI (US); Fanwen Zeng, Belle Mead, NJ (US); John W. Ashmore, Lansdale, PA (US); Boris Polanuyer, Lansdale, PA (US); Thomas Sanders, Willow Grove, PA (US); David Laganella, Swedesboro, NJ (US)

(73) Assignees: ROHM AND HAAS COMPANY, Collegeville, PA (US); DOW GLOBAL TECHNOLOGIES LLC, Midland, MI (US)

( * ) Notice: Subject to any disclaimer, the term of this patent is extended or adjusted under 35 U.S.C. 154(b) by 50 days.

This patent is subject to a terminal disclaimer.

(21) Appl. No.: 14/369,033

(22) PCT Filed: Dec. 27, 2012

(86) PCT No.: PCT/US2012/071738
§ 371 (c)(1),
(2) Date: Jun. 26, 2014

(87) PCT Pub. No.: WO2013/101887
PCT Pub. Date: Jul. 4, 2013

(65) Prior Publication Data
US 2014/0348937 A1   Nov. 27, 2014

Related U.S. Application Data

(60) Provisional application No. 61/580,447, filed on Dec. 27, 2011.

(51) Int. Cl.
*A01N 25/28* (2006.01)
*B01J 13/14* (2006.01)
*A01N 43/80* (2006.01)
*B01J 13/20* (2006.01)
*A01N 25/10* (2006.01)
*A01N 25/34* (2006.01)

(52) U.S. Cl.
CPC ............ *A01N 43/80* (2013.01); *A01N 25/10* (2013.01); *A01N 25/28* (2013.01); *A01N 25/34* (2013.01); *B01J 13/14* (2013.01); *B01J 13/206* (2013.01)

(58) Field of Classification Search
None
See application file for complete search history.

(56) References Cited

U.S. PATENT DOCUMENTS

| | | | |
|---|---|---|---|
| 4,610,927 A * | 9/1986 | Igarashi et al. | 428/402.21 |
| 6,486,099 B2 | 11/2002 | Igari et al. | |
| 2006/0063001 A1 * | 3/2006 | Hart et al. | 428/402.2 |
| 2007/0138674 A1 * | 6/2007 | Anastasiou et al. | 264/4.1 |

OTHER PUBLICATIONS

Chlorpyrifos MSDS, http://www.scbt.com/datasheet-217887-chlorpyrifos.html, retrieved online on Jun. 29, 2015.*

* cited by examiner

*Primary Examiner* — Jennifer A Berrios
(74) *Attorney, Agent, or Firm* — Tifani M. Edwards

(57) ABSTRACT

A composition is provided, comprising microcapsules, wherein said microcapsules comprise a core and an outer shell, wherein said core comprises one or more water-insoluble compound having melting point above 15° C., wherein said outer shell comprises one or more amino resin that is a reaction product of reactants comprising one or more polyamine and formaldehyde, and wherein said composition further comprises one or more formaldehyde scavenger, one or more reaction product of said amino resin with a formaldehyde scavenger, or a mixture thereof. Also provided is a method of making such a composition.

4 Claims, No Drawings

MICROCAPSULES

It is often desired to provide a microcapsule in which a water-insoluble compound is encapsulated in a shell that contains an amino resin. One reason for doing so, for example, is to provide the water-insoluble compound in a form that can be incorporated into a liquid coating composition, so that a dried layer of that liquid coating composition may be formed on a substrate, so that when the coated substrate is submerged in water, the water-insoluble compound will be gradually released into the water.

U.S. Pat. No. 6,486,099 describes a method of making microcapsules. That method involves a core material, a first coating step, and a second coating step. The second coating step involves forming a polycondensate of an amino resin prepolymer. It has been discovered that microcapsules made by the methods disclosed in U.S. Pat. No. 6,486,099 have the undesirable trait that, after the microcapsules are stored in the dry state, their ability to release the core material is diminished or eliminated. That is, after the storage in the dry state, when the microcapsules are subsequently exposed to seawater, the release of the core material is diminished or eliminated.

It is desired to provide microcapsules that maintain a useful amount of their ability to release core material, even after they have been stored in the dry state.

The following is a statement of the invention.

The first aspect of the present invention is a composition comprising microcapsules, wherein said microcapsules comprise a core and an outer shell, wherein said core comprises one or more water-insoluble compound having melting point above 15° C., wherein said outer shell comprises one or more amino resin that is a reaction product of reactants comprising one or more polyamine and formaldehyde, and wherein said composition further comprises one or more formaldehyde scavenger, one or more reaction product of said amino resin with a formaldehyde scavenger, or a mixture thereof.

The second aspect of the present invention is method of making a composition that comprises the microcapsules described in the first aspect, said method comprising making said microcapsules and then forming a mixture of said microcapsules with one or more formaldehyde scavenger.

The following is a detailed description of the invention.

As used herein, the following terms have the designated definitions, unless the context clearly indicates otherwise.

The size of a spherical particle is characterized by its diameter. For a particle that is not spherical, the "diameter" herein is the diameter of a sphere with the same volume as the particle. A shell material is said herein to "surround" a core particle if, when the object formed by the combination of the shell material and the core material is considered, that object meets the following criteria: the object contains some volume that is made of the composition of the core particle, and at least 50% or more of the surface area of the microcapsule, based the total area of the surface of the microcapsule, is made of the composition of the shell material.

A microcapsule is a particle having a core surrounded by an outer shell and having diameter of 0.1 micrometers to 200 micrometers. The composition of the outer shell is different from the composition of the core. One or more inner shell may be present in between the core and the outer shell.

A collection of particles may be characterized by d(0.5) and d(0.9). Half of the collection of particles by volume is composed of particles having diameter less than d(0.5). 90% of the collection of particles by volume is composed of particles having diameter less than d(0.9).

A compound is water-insoluble if the maximum amount of that compound that will dissolve in 100 g of water at 25° C. is 0.1 g or less. A compound is water-soluble if the amount of that compound that will dissolve in 100 g of water at 25° C. is more than 1 g.

As used herein a "resin" is a polymer. A polymer is a relatively large molecule made up of the reaction products of smaller chemical repeat units. Polymer molecular weights can be measured by standard methods such as, for example, size exclusion chromatography (SEC, also called gel permeation chromatography or GPC). Polymers have weight-average molecular weight (Mw) of 1,000 or more. Polymers may be linear, branched, star-shaped, or a mixture thereof. Polymers that are fully crosslinked are considered to have molecular weight that is infinite. Molecules that can react with each other to form the repeat units of a polymer are known herein as "monomers."

An amino resin is a polymer that is a reaction product of reactants that include of one or more aldehyde and one or more polyamine. An amine group is —NH$_2$. As used herein, a compound is considered to be an amine compound if it has an amine group, whether or not the amine group is connected to a carbonyl (i.e., whether or not the compound could also be considered to be an amide or urea compound). Some amine compounds are diamines or polyamines. A diamine is a compound having exactly two amine groups. A polyamine is a compound whose molecule has two or more amine groups.

A formaldehyde scavenger is a compound capable of reacting with formaldehyde to form a reaction product that is not formaldehyde. While the present invention is not limited to any specific mechanism, it is considered that in many embodiments an amine compound and formaldehyde will exist in equilibrium with methylol groups that are formed by the reaction of amine compound with formaldehyde. It is considered that when a formaldehyde scavenger is present, it will form a stable reaction product of itself with formaldehyde, thus removing formaldehyde from the equilibrium with methylol groups, thus shifting that equilibrium back to the amine compound and formaldehyde, thus allowing more formaldehyde to be removed, and so on. Therefore it is considered that the presence of formaldehyde scavenger can reduce the amount of methylol groups.

Also considered to be included in the category of "formaldehyde scavengers" are compounds (herein called "methylol capping compounds") that are capable of reacting with methylol groups that are formed by the reaction of formaldehyde with an amine group.

As defined herein, a compound with a reactive hydrogen is a compound having at least one of Structure I, II, III, or IV:

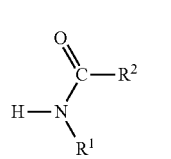

I

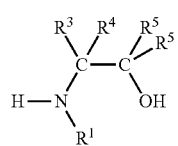

II

-continued

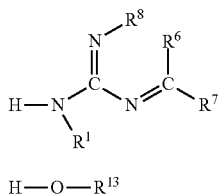

H—O—R¹³    IV

R¹, R³, R⁴, each R⁵, R⁶, and R⁷ is each independently a hydrogen or a substituted or unsubstituted amine group or a substituted or unsubstituted organic group. R² is a substituted or unsubstituted amine group or a substituted or unsubstituted organic group. R⁸ is a substituted or unsubstituted organic group. In structure I, R¹ and R² may be connected to each other to form a cycle. R⁸ may be connected to either R⁶ or R⁷ to form a cycle. R¹³ is a substituted or unsubstituted aromatic ring.

A "dispersion" is a collection of discrete particles distributed throughout a continuous medium. The particles may be solid or liquid or a mixture thereof. A dispersion is said to be a dispersion "in water" if the continuous medium is an aqueous medium. A continuous medium is "aqueous" if the composition of the continuous medium is 40% or more water, by weight based on the weight of the continuous medium. A continuous medium is "non-aqueous" if the composition of the continuous medium is less than 40% water by weight based on the weight of the continuous medium.

An amino prepolymer is a reaction product of reactants including one or more polyamine and formaldehyde. An amino prepolymer has molecular weight of less than 1,000.

A biocide is a compound that is capable of inhibiting the growth of, or killing, one or more species of bacteria, fungus, algae, or marine fouling organisms. Marine fouling organisms tend to grow on surfaces that are submerged under water and include hard and soft fouling organisms, including algae, tunicates, hydroids, bivalves, bryozoans, polychaete worms, sponges, and barnacles.

A coating composition is a composition that is capable of being applied as a layer on the surface of a substrate and capable of forming a dry layer (the "dry coating") that adheres to the surface of the substrate.

A marine coating composition is a coating composition that is capable of forming a dry coating on the surface of a marine object. After formation of the dry coating, the dry coating will adhere to the surface for a usefully long time, even when some or all of the coated surface remains under water for significant amounts of time (i.e., at least one hour per day). Marine objects are those that are put to use in environments in which some or all of the object is under water for significant amounts of time. Examples of marine objects include ships, piers, docks, pilings, fishnets, heat exchangers, dams, and piping structures, such as intake screens.

A marine coating composition that is effective at inhibiting the growth of one or more marine fouling organism is a marine anti-fouling (MAF) coating composition. A marine anti-foulant is a compound that is added to a marine coating composition and that improves the ability of the marine coating composition to inhibit the growth of one or more marine fouling organism.

A liquid composition is in the liquid state in a standard atmosphere over a temperature range that includes 0° C. to 60° C.

As used herein, when a ratio of two quantities is said to be "X:100 or more," it is meant that the ratio is Y:100, where Y is equal to or greater than X. Similarly, when a ratio of two quantities is said to be "Z:100 or less," it is meant that the ratio is W:100, where W is equal to or less than Z.

A composition that is "dry" or "dried" has total volatile compound content of 5% or less by weight based on the weight of the composition. Volatile compounds have boiling point at 1 atmosphere pressure of 200° C. or below.

The composition of the present invention comprises microcapsules. The composition of the present invention preferably has d(0.5) of 0.5 micrometer or larger; more preferably 2 micrometer or larger; more preferably 5 micrometer or larger. The composition of the present invention preferably has d(0.5) of 100 micrometer or smaller; more preferably 50 micrometer or smaller; more preferably 30 micrometer or smaller. The composition of the present invention preferably has d(0.9) of 1 micrometer or larger; more preferably 4 micrometer or larger; more preferably 9 micrometer or larger. The composition of the present invention preferably has d(0.9) of 150 micrometer or smaller; more preferably 100 micrometer or smaller; more preferably 50 micrometer or smaller.

The core of the microcapsule of the present invention may comprise any water-insoluble compound or compounds. Preferably the core contains a water-insoluble compound that has solubility in water at 25° C. of 0.05 gram or less per 100 grams of water; more preferably 0.01 gram or less per 100 grams of water. Preferably the core contains one or more water-insoluble compound having melting point of 20° C. or higher; more preferably 35° C. or higher. Preferably the core contains one or more water-insoluble compound having melting point of 200° C. or lower; more preferably 100° C. or lower; more preferably 75° C. or lower.

Preferably, the total amount of water-soluble compounds in the core is either zero or is less than 1% by weight based on the weight of the core.

Preferably the core contains one or more biocide. Preferred biocides are water-insoluble derivatives of 4-isothiazolin-3-one. More preferred is 4,5-dichloro-2-n-octyl-4-isothiazolin-3-one (DCOIT).

The outer shell of the microcapsule contains one or more amino resin. The amino resin preferably contains a reaction product of reactants that include one or more amine compound and, optionally, one or more phenolic compound. Preferred amine compounds are urea, melamine, benzoguanamine, glycoluril, and mixtures thereof. More preferred are urea and melamine. Preferred phenolic compounds are phenol, substituted phenols, resorcinol, substituted resorcinols, and mixtures thereof. More preferred phenolic compound is resorcinol. More preferred amine resins contain a reaction product of reactants that include urea, melamine, resorcinol, and mixtures thereof.

Preferably the amine compound contains a reaction product of reactants that include one or more amine compound and one or more amine-reactive compound. Preferred amine-reactive compounds are formaldehyde, acetaldehyde, glutaraldehyde, glyoxal, and mixtures thereof. More preferred is formaldehyde.

More preferred amino resins contain a reaction product of reactants that either include both of urea and melamine or include both of urea and resorcinol. Preferred amino resins contain a reaction product of one or more of the following combinations of reactants: melamine with formaldehyde; urea with formaldehyde; melamine and urea with formaldehyde; urea and resorcinol with formaldehyde.

Among embodiments in which the amino resin contains a reaction product of reactants that include urea and melamine, it is useful to characterize that amino resin by examining the weight ratio ("UM ratio") of urea used in making the amino resin to melamine used in making the resin. Among such embodiments, preferably the UM ratio is 50:100 or more; more preferably 75:100 or more. Among such embodiments, the UM ratio is 200:100 or less; more preferably 133:100 or less.

In preferred embodiments, the ratio of the sum of the weights of all amino resins to the weight of the core is 8:100 or more; more preferably 15:100 or more. In preferred embodiments, the ratio of the sum of the weights of all amino resins to the weight of the core is 60:100 or less; more preferably 50:100 or less; more preferably 40:100 or less.

The composition of the present invention contains one or more formaldehyde scavenger, one or more reaction product of the amino resin with a formaldehyde scavenger, or a mixture thereof. If one or more reaction product of the amino resin with a formaldehyde scavenger is present, it is preferred that one or more formaldehyde scavenger is also present, and it is preferred that some or all of the reaction product is the reaction product of formaldehyde with a formaldehyde scavenger that is also present in the composition. Preferred formaldehyde scavengers are compounds with at least one reactive hydrogen.

When a compound of structure I is used, preferred are urea, (meth)acrylamides, and compounds of structure V:

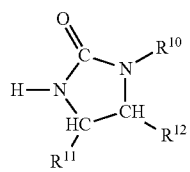

V $R^{10}$ is hydrogen, $C_1$-$C_6$ alkyl, or alkyloxy. $R^{11}$ and $R^{12}$ are independently hydrogen, hydroxyl, amine, —$NHR^{14}$ (where $R^{14}$ is $C_1$-$C_6$ alkyl, alkyloxy, or alkylamine), or carboxyl. Preferred compounds of structure V are ethylene urea ($R^{10}$, $R^{11}$, and $R^{12}$ are all hydrogen) and dihydroxy ethylene urea (DHEU; $R^{10}$ is hydrogen; $R^{11}$ and $R^{12}$ are hydroxyl).

(Meth)acrylamides include acrylamide, methacrylamide, N-substituted acrylamide, and N-substituted methacrylamide. Preferred (meth)acrylamide is N-methylol acrylamide.

When a compound of structure II is used, preferred are those of type IIa and type IIb. Compounds of type IIa have $R^1$ that is —$CH_2CH_2OH$. Preferred compound of type IIa is diethanolamine. Compounds of type IIb have the following: $R^1$ is hydrogen, both $R^5$s are hydrogen, and $R^3$ is methyl, ethyl, or —$CH_2OH$, and $R^4$ is methyl or —$CH_2OH$. When $R^3$ is methyl and $R^4$ is —$CH_2OH$ the compound is called "AMPD", when $R^3$ is ethyl and $R^4$ is —$CH_2OH$ the compound is called "AEPD", and when $R^3$ and $R^4$ are both methyl the compound is called "AMP". The preferred compound of type IIb is a compound herein called "TRIS," in which $R^1$ is hydrogen, both $R^5$s are hydrogen, and both $R^3$ and $R^4$ are —$CH_2OH$.

When a compound of structure III is used, preferred is melamine.

When a compound of structure IV is used, preferred are compounds in which one or more hydroxyl group in addition to the one shown in structure IV is present. More preferred is resorcinol.

When a methylol capping compound is used, preferred methylol capping compounds have the structure VI:

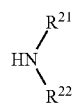

VI $R^{21}$ and $R^{22}$ are each independently hydrogen or any organic group; at least one of $R^{21}$ and $R^{22}$ is not hydrogen; $R^{21}$ and $R^{22}$ are optionally joined together to form a cycle. Preferably, either $R^{21}$ and $R^{22}$ are joined to form a cyclic group having 4 to 8 members in which each member is either a —$CH_2$— group or an —NH— group or else each of $R^{21}$ and $R^{22}$ is independently hydrogen or an alkyl group having 1 to 4 carbon atoms. Preferred methylol capping compounds are piperazine, diethylamine, dimethylamine, ethylamine, methylamine, and mixtures thereof. While the present invention is not limited to any specific mechanism, it is considered that in many embodiments a methylol capping compound operates by the following reaction:

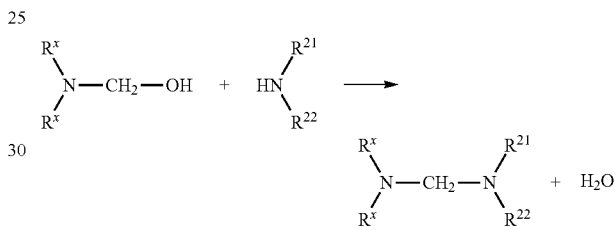

Where each Rx is independent and is determined by the amine compound that reacted with formaldehyde to form the methylol group. It is considered that the group N—$CH_2$—N is relatively stable and will not react further under the conditions of practicing the present invention.

Preferred formaldehyde scavengers are urea, dimethylurea, ethylene urea, DHEU, AMP, AMPD, AEPD, TRIS, melamine, resorcinol, N-methylol acrylamide, diethanolamine, and mixtures thereof; more preferred are urea, dimethylurea, ethylene urea, DHEU, TRIS, melamine, resorcinol, N-methylol acrylamide, diethanolamine, piperazine, diethylamine, dimethylamine, and mixtures thereof; more preferred are urea, ethylene urea, TRIS, melamine, resorcinol, N-methylol acrylamide, diethanolamine, and mixtures thereof; more preferred are urea, ethylene urea, TRIS, and mixtures thereof; more preferred are urea, ethylene urea, and mixtures thereof.

It is useful to consider the reaction product of a formaldehyde scavenger with formaldehyde or with a methylol group. It is noted that such a reaction product could be either part of or not part of an amino resin. It is useful to characterize the amount of such reaction product by the formaldehyde reactant equivalent weight. As used herein, the formaldehyde reactant equivalent weight is the weight of formaldehyde scavenger that reacted with formaldehyde or with the methylol group to form the reaction product. In compositions of the present invention, it is preferred that the sum of the weight of formaldehyde scavenger plus the formaldehyde reactant equivalent weight is preferably, based on the total weight of the composition, 1% or more; more preferably 2% or more; more preferably 5% or more; more preferably 10% or more. In compositions of the present invention, it is preferred that the sum of the weight of formaldehyde scavenger plus the formaldehyde reactant equivalent weight is preferably, based on the total weight of the composition, 50% or less; more preferably 30% or less.

The composition of the present invention may be made by any method. Preferred are methods in which microcapsules are formed and then mixed with one or more formaldehyde scavenger. More preferred are methods in which a dispersion of microcapsules in water is formed; one or more formaldehyde scavenger is added to that dispersion; and then the dispersion is dried.

Among embodiments in which a dispersion of microcapsules in water is formed, any method may be used for making such a dispersion. Two suitable methods are described herein as method A and method B. Preferred is method B.

Method A involves making a dispersion D-A. Making dispersion D-A involves an ethylene copolymer (i.e., a copolymer of ethylene with a polar monomer such as, for example, maleic anhydride), a basic reagent (e.g., KOH), core material, and a crosslinker. The ethylene copolymer, basic reagent, and core material are mixed together, preferably in a high-speed mixer, to make D-A. One or more shell of urea/resorcinol/formaldehyde is then formed on the droplets of dispersion D-A. Further description of method A may be found in U.S. Pat. No. 7,550,200.

When performing method B, it is preferred to proceed by a process that includes making a dispersion of the water-insoluble compound in water; such dispersion is herein called "dispersion (I)." Preferably the process also involves making a mixture (herein called "mixture (III)") that contains dispersion (I) and also contains one or more amino prepolymer (herein called "amino prepolymer (II)"). Preferably, a reaction is performed on mixture (III) to form one or more amino resin.

A preferred method of making dispersion (I) is as follows. An aqueous medium is provided at a temperature above the melting point of the water-insoluble compound. The amount of water in the aqueous medium, by weight based on the weight of the continuous medium, is preferably 40% or more; more preferably 50% or more. Preferably the aqueous medium contains one or more coacervation agent (herein labeled "CA"). Preferably, CA is water-soluble. Preferably, CA is cationic (i.e., when dissolved in water, CA has a positive charge at a range of pH values that falls within or overlaps the range pH=4 to pH=8). Preferably, CA is an amino resin, an amino prepolymer, or a mixture thereof. Preferably, CA contains a reaction product of reactants that contain one or more activated polyamine, formaldehyde, and, optionally, one or more diamine. More preferably, CA contains a reaction product of reactants that contain urea, formaldehyde, and one or more diamine selected from diethylenetriamine, triethylenetetramine, tetraethylenetriamine, or guanidine.

Preferably, water-insoluble compound is provided in liquid form. If the melting point of the water-insoluble compound is above 25° C., the water-insoluble compound is preferably heated above its melting point and then used in liquid form. Preferably the water-insoluble compound, in liquid form, is added to the aqueous medium.

Preferably, the ratio of the weight of water-insoluble compound to the weight of water in dispersion (I) is 20:100 or more; more preferably 35:100 or more. Preferably, the ratio of the weight of water-insoluble compound to the weight of water in dispersion (I) is 70:100 or less; more preferably 60:100 or less.

Preferably, one or more emulsion stabilizer is also added to the aqueous medium. Emulsion stabilizers include polymeric stabilizers, nonionic surfactants, and anionic surfactants. Preferred are anionic surfactants.

Among embodiments in which CA and emulsion stabilizer are both used, it is contemplated that spherical droplets of water-insoluble compound are formed that are coated with a mixture of CA and emulsion stabilizer. Preferably, these spherical droplets have d(0.5) of 0.1 micrometer to 100 micrometer.

Preferably, two different amino prepolymers (herein called "PPU" and "PPM") are prepared and then are mixed with dispersion (I). Preferably, PPU is a reaction product of reactants that contain urea and formaldehyde. Preferred ratio of moles of formaldehyde to moles of urea is 50:100 or higher; more preferably 80:100 or higher; more preferably 110:100 or higher. Preferred ratio of moles of formaldehyde to moles of urea is 300:100 or lower; more preferably 250:100 or lower; more preferably 200:100 or lower.

Preferably, PPU is made by mixing urea, formaldehyde, and water. The preferred ratio of the sum of the weight of urea plus the weight of formaldehyde to the weight of water is 30:100 or higher; more preferably 60:100 or higher. The preferred ratio of the sum of the weight of urea plus the weight of formaldehyde to the weight of water is 140:100 or lower; more preferably 85:100 or lower. Preferably, the pH of the mixture of urea, formaldehyde, and water is adjusted by addition a basic reagent. Preferably, after addition of basic reagent, the pH of the mixture is 7 to 9. Preferably, after addition of the basic reagent, the mixture is maintained at a temperature of 30° C. to 95° C. for 10 minutes to 3 hours. It is contemplated that some or all of the urea will react with some or all of the formaldehyde; the result, including the reaction product, the remaining urea (if any), and the remaining formaldehyde (if any) is considered the PPU. The mixture that results, which includes PPU, water, and basic reagent, is herein called the "PPU mixture."

Preferably, PPM is a reaction product of reactants that contain melamine and formaldehyde. Preferred ratio of moles of formaldehyde to moles of melamine is 80:100 or higher; more preferably 150:100 or higher; more preferably 220:100 or higher. Preferred ratio of moles of formaldehyde to moles of melamine is 450:100 or lower; more preferably 400:100 or lower; more preferably 350:100 or lower.

Preferably, PPM is made by mixing melamine, formaldehyde, and water. The preferred ratio of the sum of the weight of melamine plus the weight of formaldehyde to the weight of water is 10:100 or higher; more preferably 25:100 or higher. The preferred ratio of the sum of the weight of melamine plus the weight of formaldehyde to the weight of water is 100:100 or lower; more preferably 75:100 or lower; more preferably 50:100 or lower. Preferably, the pH of the mixture of melamine, formaldehyde, and water is adjusted by addition a basic reagent. Preferably, after addition of basic reagent, the pH of the mixture is 7 to 9. Preferably, after addition of the basic reagent, the mixture is maintained at a temperature of 30° C. to 80° C. for 10 minutes to 3 hours. It is contemplated that some or all of the melamine will react with some or all of the formaldehyde; the result, including the reaction product, remaining melamine (if any), and remaining formaldehyde (if any) is considered the PPM. The mixture that results, which includes PPM, water, and basic reagent, is herein called the "PPM mixture."

Preferably, PPU and PPM are added to dispersion (I). Preferably the PPU and PPM are either mixed together and then added to dispersion (I) or are added separately to dispersion (I), either simultaneously or sequentially or a combination thereof. After PPU and PPM have been added to dispersion (I), an acidic reagent is preferably added to the resulting mixture. Preferred acidic reagents have pKa of 5.0 or lower. Preferred acidic reagents are acetic acid, formic acid, hydrochloric acid, sulfuric acid, phosphoric acid, para-toluenesulfonic acid, and citric acid. After addition of the acidic reagent, the pH of the mixture is preferably 4.25 to 5.25. Preferably the mixture is then maintained at 35° C. to 70° C. for 30 minutes to 6 hours. Then, preferably, additional acidic reagent is added to bring the pH to 1.8 to 3.3, and then, the mixture is preferably maintained at 35° C. to 70° C. for 8 to 36 hours.

Many methods of making the microcapsules, including method A and method B, involve making an emulsion of the core material and other ingredients in water. Preferably, the emulsion includes one or more stabilizer. Stabilizers may be surfactants or may be polymeric stabilizers. Preferred surfactants are anionic surfactants. Preferred polymeric stabilizers are coacervation shells, polyvinyl alcohols, copolymers of ethylene and maleic anhydride, polyvinyl pyrrolidone, polystyrene sulfonic acid, and mixtures thereof. Preferably the process of forming the emulsion is performed with a high-speed mixer such as a homogenizer operating at high rotation rate of 1,000 rpm or higher. Homogenization may be performed as a batch process or by an inline process (inline processes may be single pass or may involve multiple passes through the homogenizer). Ingredients may be fed to the mixer as a single mixed stream or may be simultaneously fed as separate streams.

Preferably, after microcapsules are made, the microcapsules and one or more formaldehyde scavenger are mixed together (i.e., brought together to form a mixture). The microcapsules may be mixed with formaldehyde scavenger at any time after the microcapsules are formed. More preferably, the microcapsules are made as a dispersion in water, the microcapsules are filtered to form a wetcake, that wetcake is then redispersed in water, then the re-dispersed microcapsules are mixed together with one or more acid scavenger, and then the mixture is dried. Preferably, the amount of formaldehyde scavenger that is mixed with the microcapsules is, by weight based on the weight of the mixture, 5% or more; more preferably 10% or more.

It is contemplated that in some embodiments, the process of making the microcapsules may result in a relatively small amount (2% or less by weight, based on the weight of the microcapsules) of one or more formaldehyde scavenger. For example, some urea might be present in the microcapsules because some of the urea used in making the microcapsules did not react. In such embodiments, it is preferred that further formaldehyde scavenger be mixed with the microcapsules after the microcapsules are made.

Preferably the microcapsules are dried. Preferably the amount of water in the dried microcapsules is, by weight based on the weight of the composition, 5% or less; more preferably 2% or less.

Drying may be performed by any method, including, for example, air drying, tumble drying, spray drying, and combinations thereof. The preferred method of drying is spray drying.

When formaldehyde scavenger is mixed with microcapsules, that mixing is preferably performed either while the microcapsules are in an aqueous dispersion or after the microcapsules have been dried. More preferably, that mixing is performed while the microcapsules are in an aqueous dispersion, and the resulting mixture is then dried.

Preferably the composition of the present invention is dried. After drying, the composition may be used for a wide variety of purposes. Preferably the dried composition is mixed with other ingredients to form a non-aqueous liquid coating composition. A liquid coating composition has the following characteristics: it is in the liquid state at a range of temperatures that includes 15° C. to 40° C.; it contains one or more coating binder; and it contains one or more pigment. A coating binder is a substance that is capable of forming a film; that is, when the binder is present in a liquid coating composition, when that composition is applied as a layer on a substrate and then dried or allowed to dry at ambient temperature (which may be any temperature from 0° C. to 45° C.) to form a dry coating, the binder is capable of forming a continuous film in that dry coating. Preferred binders are soluble in the continuous liquid medium of the coating composition. Preferred binders contain one or more rosin, one or more polymer, or a mixture thereof. Preferred rosins include unmodified rosin and alkylated rosin esters. Preferred polymers include silicone polymers, silicone acrylic polymers, and acrylic resin acid salts; more preferred are zinc and copper salts of acrylic resin acids. Acrylic resin acids are a group of related thermoplastic or thermosetting plastic substances derived from acrylic acid, methacrylic acid or other related compounds. A pigment is a particulate solid. A pigment is solid over a temperature range that includes the range −10° C. to 95° C. Preferred pigments have weight-average diameter of the particles of 0.2 micron to 10 micron.

When dried composition of the present invention is used in making a liquid coating composition, the composition of the present invention becomes dispersed in the continuous medium of the coating composition. Preferably the amount of the composition of the present invention, by weight based on the weight of the liquid coating composition, is 1% or more; more preferably 2% or more. Preferably the amount of the composition of the present invention, by weight based on the weight of the liquid coating composition, is 15% or less; more preferably 10% or less.

Coating compositions that contain the composition of the present invention are preferably marine coating compositions; more preferably are marine anti-fouling coating compositions.

The following are examples of the present invention.

General Procedure for Microcapsule Preparation

Microcapsules were prepared as described in U.S. Pat. No. 6,486,099. The biocide active 4,5-Dichloro-2-n-octyl-4-isothiazolin-3-one (DCOIT) (235 g) was melted immediately prior to the kettle preparation. Water was added into the kettle equipped with mechanical mixing device, temperature control device and inlet/outlet pumping lines. The kettle was heated to 50° C. Then 33.8 g of a solution of U-Ramin™ P-1500 cationic urea-formaldehyde pre-polymer (concentration 40% by weight, based on the weight of the solution) in water (from Mitsui Kagaku K.K.), was added to the kettle followed by addition of triethanolamine and pH adjustment with citric acid. Immediately, melted DCOIT and the aqueous solution of sodium dodecylbenzene sulfonate, were added to the kettle with mixing. The coarse emulsion was emulsified by pumping through a Silverson in-line mixer or IKA Magic Lab™ mixer (from IKA).

Independently, melamine formaldehyde (MF) and urea formaldehyde (UF) pre-polymers were prepared. To one kettle equipped with mechanical mixing device, temperature control device and addition port was added water, 21.5 g of melamine, and 55.4 g of a solution of formaldehyde in water (concentration 37% by weight, based on the weight of the solution) whose pH was pre-adjusted to 8 with 20% triethanolamine aqueous solution. The mixture was heated to 50° C. with mixing. After the temperature reached 50° C., (about 12 min), it took another 28 min for the melamine to dissolve completely. After another 30 minutes at 50° C., the clear pre-polymer solution was then cooled and ready for use immediately for the next step of the process. Similarly, to another kettle equipped with mechanical mixing device, temperature control device and addition port was added water, 22.1 g of urea, and 53.8 g of a solution of formaldehyde in water (concentration 37% by weight, based on the weight of the solution) whose pH was pre-adjusted to 8 with 20% triethanolamine aqueous solution. The mixture was heated to 70° C. with mixing. After the temperature reached 70° C., (about 9 min), the clear solution was mixed at this temperature for 51 min. After that, the pre-polymer was cooled and ready for use immediately for the next step of process.

At the end of prepolymer preparation, MF and UF prepolymers were added to the DCOIT in water emulsion as prepared above in 10 minutes. The temperature was maintained at 50° C. The mixture pH was adjusted to 4.75 with 10% citric acid aqueous solution. Pre-heated water was then added to the reaction mixture to reduce solution viscosity. After mixing at 50° C. for 2.5 hr, the reaction slurry was adjusted to pH 2.8 with 30% citric acid aqueous solution. At 0.5 and 2.5 hr after pH adjustment, pre-heated water was added to the kettle to reduce the viscosity. The reaction slurry was mixed at 50° C. overnight, about 19 hr after pH adjustment to 2.8. Then the slurry was cooled to 30° C. Solid ammonium chloride was added to the kettle followed, 10 minutes later, by the addition of 25% sodium hydroxide aqueous solution so that the pH of slurry was adjusted to 7. After another 10 minutes, the slurry pH dropped, and the pH was adjusted again to 7. The slurry was then passed through a 100 mesh screen to remove gel. The filtrate, which can settle quickly, was subjected to Buchner filtration. The wetcake on the Buchner funnel was subjected to three slow plug flow washes in order to reduce salt content. The wetcake was re-dispersed in water and then dried by spray drying.

Spray-drying of Microcapsules:

Microcapsule wetcake was redispersed in water via gentle mixing for 30 min Target slurry solids was 20%. Resulting slurry was pumped to a Buchi™ spray dryer (from Buchi). The inlet temperature was set at 155° C., while the outlet temperature was set at 77° C. Vacuum pressure was set at 20 mmHg, Atomizing gas was set at 600 L/hr. Dry powder was collected in the cyclone.

Measurement of Resistance of Active Release from Microcapsules in Solvents (Solvent Stability)

0.6 grams of capsules were placed into 100 mL autoclave bottle. 50 grams of 40% MIBK/60% Xylene (prepared wt/wt) was added to the bottle. After 1 hour, a sample was removed and labeled "Day 0." The bottle was then placed in the oven set at 50° C. Samples were taken at Days 1, 3 or 4, 7, 14, 21, 28, 56, and 84. For each sample, 20.0 microliter of the solvent layer was removed from the bottle by pipette and place into a 3 mL syringe with 0.2 micrometer filter. Next, 980 mL acetonitrile (ACN) was added by pipette to the 3 mL syringe, and the mixture was filtered into an autosampler vial. The DCOIT content in each autosampler vial was measured by HPLC.

The % DCOIT released is calculated by the following equation:

% $DCOIT$ released=100%×50 (dilution factor)×(ppm of $DCOIT$ in the vial)/(loaded level of $DCOIT$)

where loaded level of $DCOIT$=Total DCOIT from microcapsule×(weight of capsules)/(weight of solvent).

The number for "solvent stability" shown in the Table below is the percentage of DCOIT released after 28 days, based on the initial amount of DCOIT in the sample.

Measurement of Seawater Release (REL) and Seawater Release Rate (SWRR)

Synthetic seawater was prepared by adding 4.00 mL of a 6 g/L Copper Sulfate pentahydrate solution to 4 liters of Ricca™ seawater (ASTM D1141 Substitute Ocean Water without heavy metals, available from Ricca chemicals). 1986.6 grams of this solution was mixed with 13.4 grams of Dowfax™ 2A1 surfactant (from Dow Chemical Co.), mixed for 5 minutes and then filtered through a 0.2 micrometer filter.

0.02 grams of microcapsules were placed into a 118 ml (4 oz) bottle, and 100 g synthetic seawater was added into the same bottle. The bottle was then placed in the shelf at room temperature for release study. Samples were removed days 1, 3 or 4, 7, 14, 21, 28, 42, 56, 70, 84, 98, 112, 140, 168.

Sampling procedure: 1.000 mL by pipette was taken from the bottle (bottle was not agitated before sampling) and placed into an autosampler vial, then 1.000 mL was taken by pipette of fresh synthetic seawater and added back to the bottle to keep constant volume.

% DCOIT released (REL) was calculated by the following equation:

REL=100%×(ppm of $DCOIT$ in the autosampler vial)/(the loaded level of active)

where the loaded level of active=(Total $AI$ from microcapsule)×(weight of capsules)/(weight of seawater)

% DCOIT released was plotted versus Day in solution. Seawater release rate is the slope of the data at Day x (subtracting Day 1). Sea water release rate (SWRR) was calculated by the following equation:

SWRR=(REL at day 28−REL at day 1)/27

Measurement of Retention of SWRR after Heat-Ageing 10 g of microcapsules were placed in a closed vial, which was then placed in an oven at 80° C. for 1 day. The SWRR was measured as described in example 3. The retention of SWRR after heat-aging (RET) is calculated by the following equation:

RET=100*(SWRR of the heat-aged capsules/SWRR of the fresh capsules)

Particle Size Distribution (PSD) Measurement

The PSD was measured with a Malvern Mastersizer™ 2000 instrument (from Malvern) with 2000 μP Module. The spray-dryed powder was dispersed in xylene and measurement was performed with further dilution in xylene in the detection cell. Particle size d(0.5), and d(0.9) were reported.

Microcapsules with addition of additive.

Procedure of spray-drying of microcapsules with addition of additives:

Each additive was dissolved in water with the amount as described in the table based on the final powder weight. Microcapsule wetcake was redispersed in the additive solution by agitation for 30 minutes. The amount of microcapsule wetcake in the resulting slurry was 20% by weight based on the weight of the slurry.

The slurry was pumped to a Buchi™ spray dryer and dried. The inlet temperature was set at 155° C., while the outlet temperature was set at 77° C. Vacuum pressure was set at 20 mmHg Atomizing gas was set at 600 L/hr. Dry powder was collected in the cyclone.

For Comparative example C1, no additive was used. For Example 19, Comparative Example C1 was prepared and dried, and then the additive was mixed with the dry powder.

Examples 16 and 17 are comparative examples because those additives are not formaldehyde scavengers.

All samples, including comparative examples, had acceptable particle size. D(0.5) values ranged from 10.0 micrometers to 25.8 micrometers, and d(0.9) values ranged from 17.1 micrometers to 49.5 micrometers.

Definitions of the Examples and the results for PSD and Solvent Stability are shown in Tables IA and IB:

TABLE IA

| Ex. No. | Additive | Additive Amount | d(0.5) | d(0.9) | Solvent Stability |
|---|---|---|---|---|---|
| C1 | none | 0 | 11.9 | 18.1 | 1.2 |
| 2 | urea | 5% | 10.4 | 17.3 | |
| 3 | urea | 10% | 19.0 | 36.1 | |
| 4 | urea | 15% | 25.2 | 48.5 | 5.0 |
| 5 | urea | 20% | | | 1.2 |
| 6 | ethylene urea | 5% | 10.0 | 17.1 | |
| 7 | ethylene urea | 10% | 12.8 | 21.8 | 3.2 |
| 8 | ethylene urea | 15% | 13.0 | 22.8 | 2.1 |
| 9 | TRIS | 20% | 25.8 | 49.5 | 2.2 |
| 10 | N-methylolacrylamide | 20% | 11.7 | 17.6 | 77.4 |

TABLE IB

| Ex. No. | Additive | Additive Amount | d(0.5) | d(0.9) | Solvent Stability |
|---|---|---|---|---|---|
| 11 | sodium bisulfate | 20% | 13.4 | 23.4 | 1.6 |
| 12 | melamine | 1.5% | | | 1.9 |
| 13 | resorcinol | 5% | | | 1.9 |
| 14 | resorcinol | 15% | | | 46.8 |
| 15 | diethanolamine | 15% | 16.5 | 28.4 | 41.9 |
| C16 | methyl cellulose | 2.5% | 13.6 | 21.8 | 1.8 |
| C17 | PVA[1] | 2.5% | 12.8 | 19.0 | 1.7 |
| 18 | urea TRIS | 2.5% 2.5% | 22.0 | 43.5 | 1.9 |
| 19 | post added ethylene urea | 15% | | | 2.1 |

[1]poly(vinyl alcohol)

Each sample was divided into two portions. One portion ("fresh") was kept at ambient temperature (between 18° C. and 25° C.), and the other portion ("heat-aged") was stored at 80° C. for one day. Seawater release rates are shown in tables IIA and IIB.

TABLE IIA

| Ex No. | fresh REL day 1 | fresh REL day 28 | fresh SWRR | heat-aged REL day 1 | heat-aged REL day 28 | heat-aged SWRR | RET % |
|---|---|---|---|---|---|---|---|
| C1 | 3.3 | 37.1 | 1.3 | 1.2 | 1.1 | 0.0 | 0.0 |
| 2 | 3.5 | 29.1 | 0.9 | 2.8 | 4.4 | 0.1 | 6.3 |
| 3 | 3.1 | 28.9 | 1.0 | 2.7 | 6.1 | 0.1 | 13.0 |
| 4 | 4.9 | 42.8 | 1.4 | 4.2 | 16.6 | 0.5 | 32.6 |
| 5 | 2.7 | 27.3 | 0.9 | 2.6 | 17.6 | 0.5 | 52.4 |
| 6 | 3.4 | 33.8 | 1.1 | 3.1 | 8.3 | 0.2 | 17.2 |
| 7 | 3.6 | 35.1 | 1.2 | 3.0 | 9.6 | 0.2 | 21.0 |
| 8 | 2.4 | 34.4 | 1.2 | 2.9 | 17.1 | 0.5 | 44.5 |
| 9 | 7.3 | 55.8 | 1.8 | 3.7 | 14.4 | 0.4 | 22.1 |
| 10 | 5.3 | 46.7 | 1.5 | 4.4 | 15.7 | 0.4 | 27.3 |

TABLE IIB

| Ex No. | fresh REL day 1 | fresh REL day 28 | fresh SWRR | heat-aged REL day 1 | heat-aged REL day 28 | heat-aged SWRR | RET % |
|---|---|---|---|---|---|---|---|
| C11 | 3.5 | 35.1 | 1.2 | 0.6 | 3.0 | 0.1 | 7.4 |
| 12 | 3.2 | 23.9 | 0.8 | 2.5 | 6.9 | 0.2 | 20.3 |
| 13 | 2.3 | 24.1 | 0.8 | 1.8 | 7.4 | 0.2 | 24.8 |
| 14 | 2.9 | 24.2 | 0.8 | 2.3 | 8.4 | 0.2 | 27.3 |
| 15 | 1.8 | 26.1 | 0.9 | 1.3 | 6.2 | 0.1 | 16.6 |
| C16 | 2.2 | 23.4 | 0.8 | 1.9 | 1.8 | 0.0 | 0.0 |
| C17 | 2.2 | 21.4 | 0.7 | 1.9 | 1.9 | 0.0 | 0.0 |
| 18 | 3.0 | 38.0 | 1.3 | 2.3 | 6.4 | 0.2 | 11.6 |
| 19 | 2.3 | 30.7 | 1.1 | 2.8 | 5.9 | 0.1 | 10.8 |

All of the comparative examples had RET % of less than, 10% while all the examples of the present invention had RET % of 10% or more. Among the examples of the present invention, urea, ethylene urea, and TRIS showed good solvent stability as well as SWRR that was better than other examples of the present invention.

The invention claimed is:

1. A marine antifouling composition comprising microcapsules,
   wherein said microcapsules comprise a core and an outer shell,
   wherein said core comprises one or more water-insoluble compound having melting point above 15° C., and further wherein the core comprises 4,5-dichloro-2-n-octyl-4-isothiazolin-3-one,
   wherein said outer shell comprises one or more amino resin that is a reaction product of reactants comprising one or more polyamine, formaldehyde, and a basic reagent;
   wherein said polyamine comprises urea and melamine;
   and wherein said composition further comprises a formaldehyde scavenger additive
   wherein the additive is urea, ethylene urea, TRIS, or mixtures thereof in an amount greater than or equal to 15%.

2. A method of making a marine antifouling composition that comprises microcapsules, said method comprising making said microcapsules and then forming a mixture of said microcapsules with one or more formaldehyde scavenger additive,
   wherein said microcapsules comprise a core and an outer shell,
   wherein said core comprises one or more water-insoluble compound having melting point above 15° C., and further wherein the core comprises 4,5-dichloro-2-n-octyl-4-isothiazolin-3-one
   wherein said outer shell comprises one or more amino resin that is a reaction product of reactants comprising one or more polyamine formaldehyde, and a basic reagent;
   wherein said polyamine comprises urea and melamine;
   and wherein said composition further comprises a formaldehyde scavenger additive
   wherein the additive is urea, ethylene urea, TRIS, or mixtures thereof in an amount greater than or equal to 15%.

3. The method of claim 2 wherein said method comprises the steps of
   (i) forming a dispersion of said microcapsules in water
   (ii) adding said formaldehyde scavenger additive to said dispersion, and (iii) subsequent to steps (i) and (ii), drying said dispersion of said microcapsules.

4. The method of claim 3, wherein said drying is performed by spray drying.

* * * * *